US010874853B2

(12) United States Patent
Muessig et al.

(10) Patent No.: US 10,874,853 B2
(45) Date of Patent: Dec. 29, 2020

(54) X-RAY MARKER FOR IMPLANTABLE MEDICAL DEVICES

(71) Applicant: BIOTRONIK SE & Co. KG, Berlin (DE)

(72) Inventors: Dirk Muessig, West Linn, OR (US); Jeffrey A. von Arx, Lake Oswego, OR (US); Wantjinarjo Suwito, West Linn, OR (US); Carsten Momma, Rostock (DE); Matthias Frotscher, Rostock (DE); Marco Bosselmann, Rostock (DE)

(73) Assignee: BIOTRONIK SE & Co. KG, Berlin (DE)

( * ) Notice: Subject to any disclaimer, the term of this patent is extended or adjusted under 35 U.S.C. 154(b) by 95 days.

(21) Appl. No.: 15/998,489

(22) Filed: Aug. 16, 2018

(65) Prior Publication Data

US 2019/0054292 A1 Feb. 21, 2019

Related U.S. Application Data

(60) Provisional application No. 62/546,019, filed on Aug. 16, 2017.

(51) Int. Cl.
| | | |
|---|---|---|
| *A61N 1/05* | (2006.01) | |
| *A61N 1/378* | (2006.01) | |
| *A61B 90/00* | (2016.01) | |
| *A61N 1/372* | (2006.01) | |
| *A61N 1/375* | (2006.01) | |

(52) U.S. Cl.
CPC .............. *A61N 1/059* (2013.01); *A61B 90/39* (2016.02); *A61N 1/3787* (2013.01); *A61N 1/37205* (2013.01); *A61N 1/37518* (2017.08); *A61B 2090/3966* (2016.02); *A61N 1/0558* (2013.01)

(58) Field of Classification Search
CPC ................ A61N 1/059; A61N 1/37518; A61N 1/37205; A61N 1/3787; A61N 1/0558; A61B 90/39; A61B 2090/3966
See application file for complete search history.

(56) References Cited

U.S. PATENT DOCUMENTS

| | | | |
|---|---|---|---|
| 2012/0130461 A1 | 5/2012 | Olsen et al. | |
| 2012/0172690 A1 | 7/2012 | Anderson et al. | |
| 2014/0257444 A1 | 9/2014 | Cole et al. | |
| 2015/0306378 A1* | 10/2015 | Schmidt ................. | A61N 1/059 600/424 |
| 2016/0228716 A1* | 8/2016 | Schmidt ............... | A61N 1/3756 |

FOREIGN PATENT DOCUMENTS

WO 2016025910 A1 2/2016

OTHER PUBLICATIONS

European Search Report and Annex to the European Search Report on European Patent Application No. EP 18 18 1167.0, dated Jan. 8, 2019 (7 pages).

* cited by examiner

*Primary Examiner* — Michael W Kahelin
(74) *Attorney, Agent, or Firm* — Buchanan Ingersoll & Rooney PC

(57) ABSTRACT

An anchoring device for anchoring an implantable medical device to tissue of a patient, wherein the anchoring device comprises at least one marker that is visible when using an imaging technique such as x-ray imaging.

14 Claims, 2 Drawing Sheets

X-RAY MARKER FOR IMPLANTABLE MEDICAL DEVICES

CROSS-REFERENCE TO RELATED APPLICATIONS

This patent application claims the benefit of U.S. Provisional Patent Application No. 62/546,019, filed on Aug. 16, 2017, which is hereby incorporated by reference in its entirety.

TECHNICAL FIELD

The present invention relates to an anchoring device for an implantable medical device, particularly for an implantable cardiac pacemaker, particularly an intracardiac pacing system (IPS).

BACKGROUND

Active medical devices are usually required to have markers that allow the identification of the implant using an imaging method, particularly x-ray imaging.

Known solutions are markers in form of metal objects containing the specific tag (information, e.g., company label and letter code) that are placed in the device, either in the metal enclosure or in the lead connection header. Particularly, in known IP S's such a tag may extend along an extension plane that itself extends along the axial direction of the IPS.

A drawback of the known solution is that it is very difficult to add a marker (also denoted as identifier) into the housing of an intracardiac pacing system due to the very small enclosure containing the electronic module. Such identifier, if made of electrically conductive material, needs to be electrically insulated from the electrical module to avoid shorts. An identifier made of nonconductive material would not need to be electrically insulated from the electronic module, but would still add volume to the electronic housing.

Another drawback of the known solution is that it is orientation dependent. Unlike a traditional pacemaker, where the orientation of the pacemaker is always almost parallel to the skin, an IPS can reside in any orientation in the heart. The known solution works well if the implant is oriented so that the marker happens to be in a plane parallel to the plane of the x-ray, but it does not work at all if the marker is perpendicular to the x-ray plane. Clinically, the known solution described above may end up requiring extra x-rays taken in different orientations in order to obtain a readable marker image.

The present invention is directed at overcoming one or more of the above-mentioned problems.

SUMMARY

Thus, based on the above, it is an objective of the present invention to provide a way of improving marking of implantable medical devices, particularly in case of pacemakers (e.g., IPS).

At least this problem is solved by an anchoring device having the features of claim 1, as well as by an implantable medical device having the features of claim 12. Embodiments of these aspects of the present invention are stated in the corresponding sub claims and are described below.

According to claim 1, an anchoring device (also denoted as tine array) for anchoring an implantable medical device to human or animal tissue is disclosed, comprising a mount, and an anchor connected to the mount and protruding from the mount, wherein, according to the present invention, the mount comprises at least one marker that can be detected by an imaging method.

Particularly, a goal of the present invention is to use an already existing structure/component of the implantable medical device, here a mount of an anchor of, e.g. an IPS, with which the anchor is fixedly attached to a housing of the medical device. This mount can be modified to serve as an (e.g., radiopaque) marker which is particularly independent from an electronic housing or battery housing of the IPS. A second goal is to use a structure which can contain multiple markers in different planes so that the marker can be imaged from multiple orientations.

In one embodiment, the anchor comprises at least one anchoring tine, which is connected to the mount. Preferably, the mount also serves as a connector, to which the at least one tine is connected. Further preferred, a plurality of tines form a tine array, which is (inter)connected by the connector. In this further embodiment, the tines and the connector (preferred formed annually) are cut from a single piece of metal, preferred a super-elastic metal alloy, especially preferred Nickel based alloys like a Nickel-Titanium alloy (for example, Nitinol).

Additionally or alternatively, the anchor may be or may comprise another form of fixation, e.g. a three-dimensional structure like a scaffold (i.e., stent, basket or the like).

According to an embodiment of the anchoring device according to the present invention, the at least one marker is a radiopaque marker that is configured to be detected by an x-ray imaging method.

Further, according to an embodiment of the anchoring device according to the present invention, said at least one marker comprises a coating or a plating attached to a base material of the mount. Particularly, also the at least one anchor can comprise or can be made out of said base material.

Further, according to an embodiment of the anchoring device according to the present invention, said plating or coating comprises or is formed out of a metal, particularly gold.

Further, according to an embodiment of the anchoring device according to the present invention, said base material comprises one of: a metal, a superelastic metal, a superelastic alloy, a metal alloy comprising nickel and titanium, particularly Nitinol.

Particularly, the at least one (e.g., radiopaque) marker can be, e.g., plated onto the mount using a material which is x-ray denser than the base material (e.g., gold plating onto Nitinol).

Further, according to an embodiment of the anchoring device according to the present invention, said at least one marker comprises at least one recess or several separate recesses formed into the mount, which recess(es) represent(s) information as described above, particularly for identifying an implantable medical device, for identifying the manufacturer of an implantable medical device, and/or for indicating a spatial position/orientation of the implantable medical device at the implantation site.

Further, according to an embodiment of the anchoring device according to the present invention, said mount is an annular member. Particularly, the mount can comprise a circular shape, particularly a cylindrical shape.

Further, according to an embodiment of the anchoring device according to the present invention, said at least one marker is implemented in multiple planes, particularly so that it is visible in x-rays regardless of the orientation of the implantable medical device, particularly IPS, into which the anchoring device is integrated.

Particularly, this can be achieved by making the marker extend along the mount. Due to the curved shape of the mount/annular member, the marker extends in multiple planes. In addition or alternatively, the mount may comprise a plurality of markers which are distributed along the periphery of the mount so that each marker extends along at least one associated extension plane.

Further, according to an embodiment of the anchoring device according to the present invention, the anchor is integrally connected to the mount.

Further, according to an embodiment of the anchoring device according to the present invention, where the at least one anchor comprises a plurality of anchoring tines, which are connected to a connector, the tines are configured to move under the action of a restoring force from a first configuration in which the tines extend along an axial direction of the connector to a second configuration in which each tine comprises a hook shape for engaging a patient's tissue.

According to yet another aspect, an implantable medical device is disclosed, which device comprises an anchoring device according to the present invention.

Further, according to an embodiment of the anchoring device according to the present invention, the implantable medical device is an implantable cardiac pacemaker, particularly an intracardiac pacing system (IPS).

Particularly, according to an embodiment, the mount is electrically insulated from a housing of the implantable cardiac pacemaker (e.g., IPS), which housing particularly accommodates a battery, a pulse generator of the implantable cardiac pacemaker, or both.

Further, according to an embodiment, the mount is (e.g., mechanically) connected to an electrically insulating header of the implantable cardiac pacemaker (e.g., IPS), which header is connected to an end section of an electrically conductive electronics housing of the implantable cardiac pacemaker, which housing accommodates at least an electrical pulse generator of the implantable cardiac pacemaker. The IPS may also comprise a battery, which may comprise a separate housing, in particular welded to the electronics housing, or which may be accommodated in the electronics housing. The pulse generator in the electronics housing is powered by said battery. Particularly, the mount is thus arranged outside of an internal space of said housing which internal space accommodates said battery and particularly pulse generator.

Particularly, in an embodiment, the implantable cardiac pacemaker, particularly IPS, is configured to be implanted into a chamber of the patient's heart, particularly into the right or left ventricle or the right atrium, particularly via a catheter. Particularly, said electronics housing—and if applicable the battery housing—is a hermetically sealed housing.

Particularly, the anchoring device is arranged on the header such that the at least one anchor protrudes out of the header at a face side of the implantable medical device for fastening the implantable cardiac pacemaker (e.g., IPS) to tissue of the chamber like a ventricle or an atrium (for example in the embodiment, where the at least one anchor is at least one tine, when the at least one tine is in the second configuration). The implantable cardiac pacemaker (e.g., IPS) may comprise a pacing electrode provided, e.g., on the face side of the header, where the at least one anchor protrudes out of the header. In case, where the at least one anchor is in form of a plurality of anchoring tines, the pacing electrode may be provided on the face side of the header between the tines for applying the electrical stimulation to the heart. Regarding the pacemaker, the notion leadless means, that the pacemaker is directly implanted into or directly attached to myocardial tissue or is not implanted subcutaneously with a lead going through the vascular system to myocardial tissue.

The present invention has the following advantages compared to already existing solutions: Incorporating the at least one marker into the mount is relatively easy to manufacture. Further, also the integration into the final device (e.g., IPS) can be realized in a simple fashion. Furthermore, no additional part is required for the at least one marker. The installation space inside the header/housing increases since a separate part is not needed for the at least one marker. Particularly, the at least one marker (or said several markers) according to the present invention is/are visible regardless of axial rotation of the implantable cardiac pacemaker (e.g., IPS).

Further features, aspects, objects, advantages, and possible applications of the present invention will become apparent from a study of the exemplary embodiments and examples described below, in combination with the Figures, and the appended claims.

DESCRIPTION OF THE DRAWINGS

Further features and embodiments of the present invention shall be described below with reference to the Figures, wherein.

DETAILED DESCRIPTION

Figure 1:
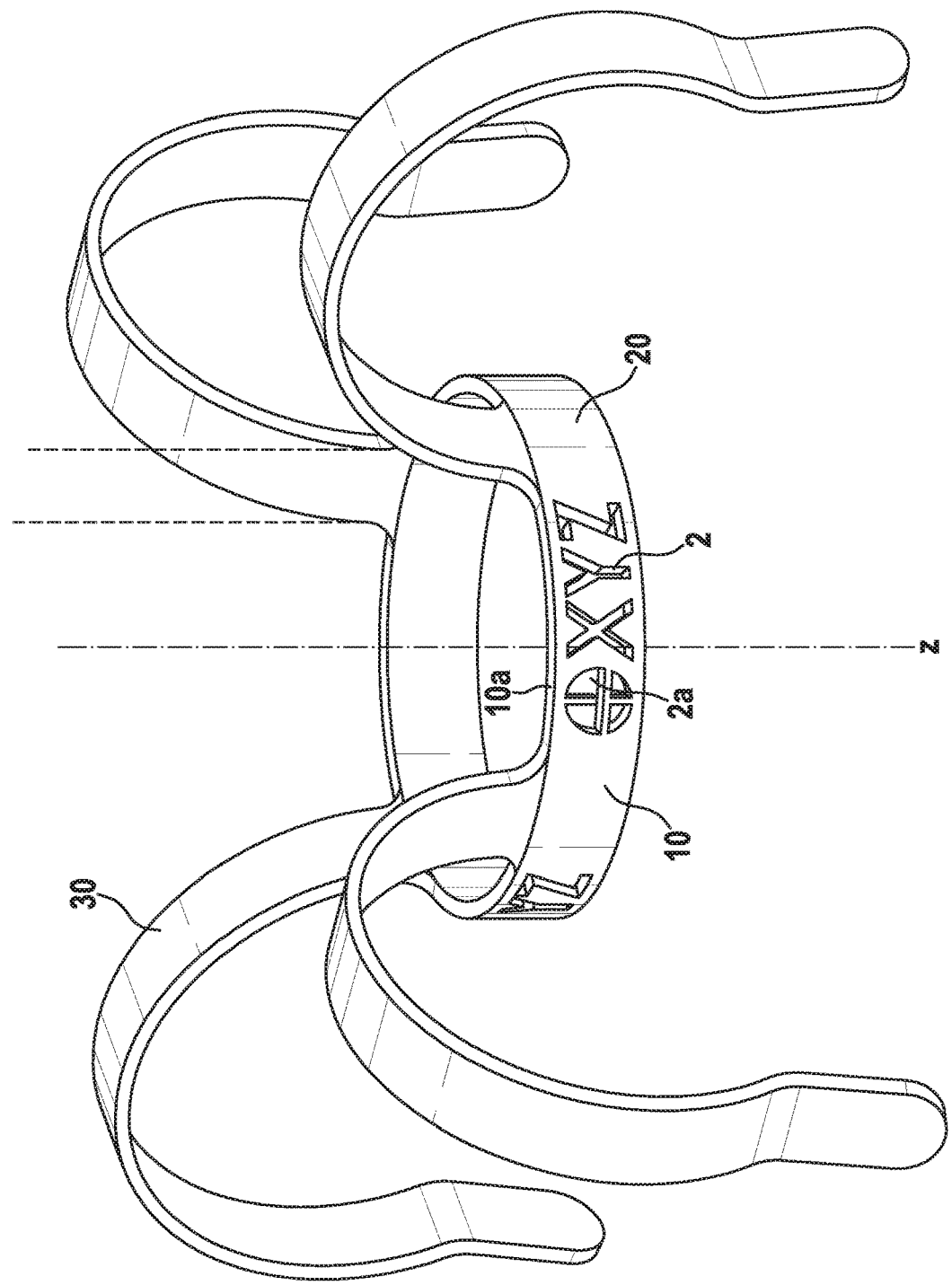
FIG. 1 shows a perspective view of an anchoring device according to the present invention.

FIG. 1 shows an exemplary embodiment of an anchoring device 1 according to the present invention for anchoring an implantable medical device 3 to tissue of a patient. In this exemplary embodiment, the anchoring device 1, which is also denoted as tine array, comprises a mount in form of a connector 10, here, e.g., in form of an annular, particularly cylindrical, member 10 and an at least one anchor in form of a plurality of elongated tines 30 connected to the connector 10 and protruding from the connector 10. According to the exemplary embodiment, the connector 10 comprises at least one marker 2 that is visible/detectable using an imaging method, e.g., an x-ray imaging method (here the at least one marker 2 is a radiopaque marker).

Particularly, the connector 10 is integrally connected to said tines 30, here to the same (e.g., upper) edge 10a of the connector 10. Particularly, the connector 10 and the tines 30 are formed out of a base material such as a superelastic alloy comprising nickel and titanium, particularly Nitinol.

Particularly, for the anchoring function, the tines 30 are configured to move under the action of a restoring force from a first configuration in which the tines 30 extend along an axial direction z of the annular member 10 (this first configuration is indicated for one tine 30 in FIG. 1 with a dashed line) to a second configuration in which each tine 30 comprises a hook shape for engaging a patient's tissue, which hook shape is shown in FIG. 1. Particularly, each hook-shaped tine 30 bends outwards so that the tines 30 form hooks in the second configuration that can be anchored in human or animal tissue at the implantation site (e.g., heart, particularly ventricle or atrium).

Particularly, as indicated in FIG. 1 the connector 10/marker 2 can comprise a gold plating 20 to increase the contrast between the unique marker 2 and the surrounding structure.

Alternatively, it is also conceivable that the unique marker 2 is generated by plating the connector 10 with an x-ray denser material (essentially this can be seen as "negative" picture).

Furthermore, as indicated in FIG. 1, the marker 2 can comprise a recess 2a that is cut out of the connector 10. Such cut out can be generated, e.g., by laser cutting the connector 10. Again, in order to increase the contrast, the connector/ring structure 10 can be gold plated 20.

Figure 2:
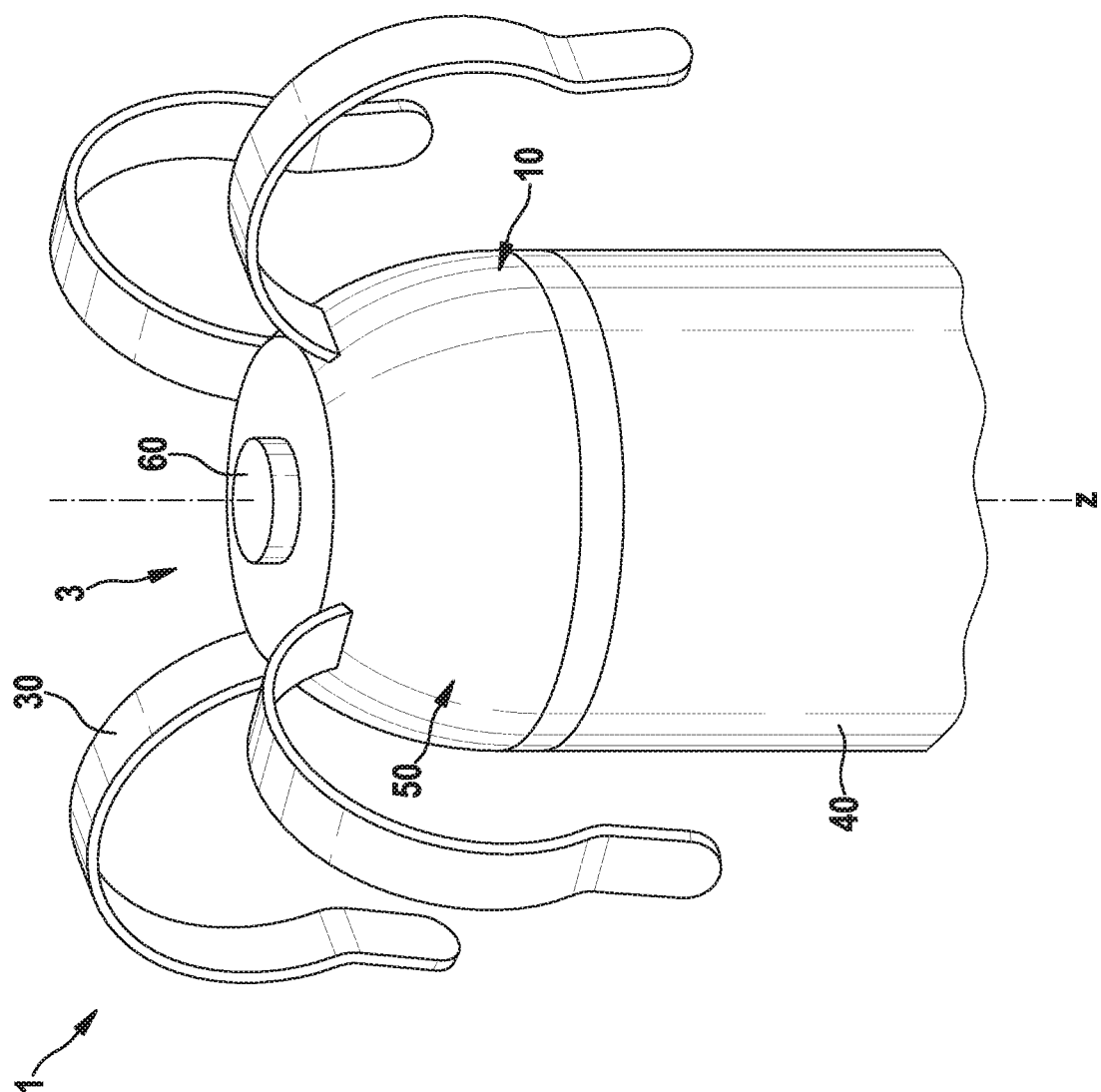
FIG. 2 shows an integration of an anchoring device according to the present invention into an implantable cardiac pacemaker, here an IPS.

FIG. 2 shows an example of a distal (tissue facing) side of a medical implant device 3 in the form of an intracardiac pacing system (IPS) 3 into which the anchoring device 1 shown in FIG. 1 is integrated. The device 3 comprises an electronics housing 40 (e.g., out of a metal) that contains at least one circuitry such as a pulse generator. The device 3 may also comprise a battery, which may comprise a separate housing (not shown), in particular welded to the electronics housing 40, or which may be accommodated in the electronics housing. A header 50, which is particularly made from a biocompatible "plastic" material (e.g., PEEK) is attached to the metal housing 40 of the implant 3. The nonconductive properties of this header 50 electrically insulate a pacing electrode 60 from the housing 40. The header 50 also serves as holding structure for the anchoring device 1. Here, particularly, the tines 30 and connector 10 can be formed out of Nitinol as a base material wherein the connector 10 may be plated as described above. The connector 10 is arranged such with respect to the header 50 that the tines 30 protrude out of the header 50 for anchoring the implant 3 to the myocardium. To ease manufacturing and to ensure that the flexible tines 30 cannot detach from the header 50 they are (e.g., integrally) connected to said annular connector 10 that is located in the header 50 of the intracardiac pacemaker 3. In one embodiment the flexible tines 30 and annular connector 10 are cut from a single piece of Nitinol.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

We claim:

1. An anchoring device for anchoring an implantable medical device to tissue of a patient, the anchoring device comprising:
   a mount; and
   at least one anchor connected to the mount and protruding from the mount,
   wherein the mount comprises at least one marker for implant identification that can be detected by an imaging method, wherein implant identification comprises identifying a manufacturer of the implant,
   wherein said at least one anchor is configured to secure the implantable medical device to the tissue of the patient, and
   wherein the mount is an annular member.

2. The anchoring device according to claim 1, wherein the at least one marker is a radiopaque marker that is configured to be detected by an x-ray imaging method.

3. The anchoring device according to claim 1, wherein said at least one marker comprises a coating or plating attached to a base material of the mount.

4. The anchoring device according to claim 3, wherein said coating or plating comprises a metal.

5. The anchoring device according to claim 3, wherein said base material comprises one of: a metal, a superelastic metal, a superelastic alloy, a metal alloy comprising nickel and titanium, Nitinol.

6. The anchoring device according to claim 1, wherein said at least one marker comprises at least one recess formed into the mount.

7. The anchoring device according to claim 1, wherein said at least one marker is implemented in multiple planes.

8. The anchoring device according to claim 1, wherein said at least one anchor is integrally connected to the mount.

9. The anchoring device according to claim 1, wherein the anchoring device comprises a plurality of markers which are distributed along the mount.

10. An implantable medical device comprising an anchoring device according to claim 1.

11. The implantable medical device according to claim 10, wherein the implantable medical device is an implantable cardiac pacemaker.

12. The implantable medical device according to claim 10, further comprising a housing, a battery and a pulse generator, wherein the mount is electrically insulated from the housing, and wherein the housing accommodates the battery, the pulse generator, or both.

13. The implantable medical device according to claim 12, further comprising an electrically insulating header, wherein the mount is connected to the header, and wherein the header is connected to said housing.

14. The implantable medical device according to claim 4, wherein the metal comprises gold.

* * * * *